United States Patent [19]

Oka et al.

[11] Patent Number: 5,462,051
[45] Date of Patent: Oct. 31, 1995

[54] MEDICAL COMMUNICATION SYSTEM

[75] Inventors: Tohru Oka, Ichinomiya; Chikao Harada, Komaki; Hidenori Suzuki, Nagoya, all of Japan

[73] Assignee: Colin Corporation, Aichi, Japan

[21] Appl. No.: 298,200

[22] Filed: Aug. 31, 1994

[51] Int. Cl.⁶ .............................. A61B 5/021; A61B 5/04
[52] U.S. Cl. ........................ 128/630; 128/904; 128/672; 128/903
[58] Field of Search ...................... 340/825.03, 825.01, 340/825.19; 128/634, 639, 630, 640, 642, 644, 670, 671, 696, 710, 715, 736, 685, 686, 903, 904; 607/122; 604/55, 53; 370/69.1, 125; 379/108

[56] References Cited

U.S. PATENT DOCUMENTS

| | | | |
|---|---|---|---|
| 4,173,971 | 11/1979 | Karz | 128/904 X |
| 4,269,193 | 5/1981 | Eckerle | 128/672 |
| 4,757,495 | 7/1988 | Decker et al. | 370/69.1 X |
| 5,138,311 | 8/1992 | Weinberg | 340/825.03 |
| 5,165,416 | 11/1992 | Shinoda et al. | 128/672 |

FOREIGN PATENT DOCUMENTS 59-77760  5/1984  Japan .

*Primary Examiner*—Lee S. Cohen
*Assistant Examiner*—Stephen Huang
*Attorney, Agent, or Firm*—Oliff & Berridge

[57] ABSTRACT

A medical communication system including (A) a sensor worn on a living body to obtain physical information of the body, and generating a signal representing the physical information; (B) a first device disposed on a side of the living body, receiving the physical information signal from (A) the sensor, and including (b1) a first transmitter which transmits the physical information signal via a communication channel, (b2) a first receiver which receives, via the communication channel, an instruction signal representing an instruction of a medical worker directed to the living body and/or an attendant person, and (b3) an output device which outputs the instruction of the medical worker so that the living body and/or attendant person receives the instruction; and (C) a second device disposed on a side of the medical worker, and including (c1) a second receiver which receives, via the communication channel, the physical information signal from (b1) the first transmitter, (c2) an output device which outputs the physical information represented by the physical information signal so that the medical worker receives the physical information, (c3) an input device which is operable for inputting the instruction of the medical worker and generates the instruction signal representing the input instruction, and (c4) a second transmitter which transmits the instruction signal via the communication channel.

14 Claims, 10 Drawing Sheets

MEDICAL COMMUNICATION SYSTEM

BACKGROUND OF THE INVENTION

1. Field of the Invention

The present invention relates to a medical communication system which transmits physical information of a living body to a medical worker distant from the living body.

1. Related Art Statement

It has been proposed a medical communication system which transmits physical information (e.g., electro-cardiogram, body temperature, blood pressure, pulse rate, etc.) of a living body such as a patient, to a medical worker such as a doctor distant from the patient, via a telephone line or by radio, so that the doctor grasps the current condition of the patient and determines appropriate medical treatments for the patient. The communication system is versatile particularly in the field of emergency medical services where immediate medical treatments are necessary and in the field of at-home medical services where patients are monitored at their homes.

If the doctor can directly give instructions to the patient and/or an attendant person for the patient, the patient and/or attendant person will be able to take provisional medical treatments for the patient. However, the above-identified communication system cannot transmit an instruction signal (e.g., sound signal representing the instructive voice of the doctor) in addition to a physical information signal representing the physical information of the patient. For transmitting the instructions of the doctor to the patient and/or attendant person concurrently with the transmission of physical information of the patient to the doctor, another communication system is necessary which transmits the instructions of the doctor to the patient and/or attendant person via a communication channel different from that used for the transmission of the physical information of the patient to the doctor.

SUMMARY OF THE INVENTION

It is therefore an object of the present invention to provide a medical communication system which transmits physical information of a living body to a medical worker and additionally transmits instructions of the medical worker to the living body and/or an attendant person for the living body, via a common communication channel.

The above object has been achieved by the present invention. According to a first aspect of the present invention, there is provided a medical communication system for transmitting physical information of a living body to a medical worker, comprising: (A) a physical information sensor device which is adapted to be worn on the living body to obtain the physical information of the living body, and generates a physical information signal representing the obtained physical information; (B) a first signal transmitting and receiving device which is adapted to be disposed on a side of the living body, receives the physical information signal from (A) the physical information sensor device, and includes (b1) a first signal transmitter which transmits the physical information signal via a communication channel, (b2) a first signal receiver which receives, via the communication channel, an instruction signal representing an instruction of the medical worker directed to at least one of the living body and an attendant person for the living body, and (b3) an instruction output device which outputs the instruction of the medical worker represented by the instruction signal received by (b2) the first signal receiver, so that the at least one of the living body and the attendant person receives the instruction; and (C) a second signal transmitting and receiving device which is adapted to be disposed on a side of the medical worker, and includes (c1) a second signal receiver which receives, via the communication channel, the physical information signal from (b1) the first signal transmitter, (c2) a physical-information output device which outputs the physical information of the living body represented by the physical information signal received by (c1) the second signal receiver, so that the medical worker receives the physical information, (c3) an instruction input device which is operable for inputting the instruction of the medical worker and generates the instruction signal representing the input instruction of the medical worker, and (c4) a second signal transmitter which transmits via the communication channel the instruction signal to (b2) the first signal receiver.

In the medical communication system in accordance with the first aspect of the present invention, the transmission of physical information of the living body (e.g., patient) and the transmission of instructions of the medical worker (e.g., doctor) are effected via the common communication channel. Even though the doctor may be at, for example, a hospital distant from the patient, for example, at his or her home or in an ambulance car, the doctor can receive the physical information (e.g., electrocardiogram) of the patient and additionally give instructions to the patient and/or attendant person. The doctor can grasp the current condition of the patient and determine appropriate medical treatments for the patient. Since the doctor directly gives instructions to the patient and/or attendant person, the patient and/or attendant person will be able to take provisional medical treatments before they are too late in case of emergency.

According to a second aspect of the present invention, there is provided a medical communication system for transmitting physical information of a living body to a medical worker, the physical information being obtained by a physical information sensor adapted to be worn on the living body, the physical information sensor generating a physical information signal representing the obtained physical information, the medical communication system comprising: (A) a first signal transmitting and receiving device which is adapted to be disposed on a side of the living body, receives the physical information signal from the physical information sensor, and includes (a1) a first sound detector which detects a first voice of at least one of the living body and an attendant person for the living body, directed to the medical worker, and generates a first sound signal representing the detected first voice, (a2) a signal mixer which mixes the physical information signal and the first sound signal into a mixture signal, (a3) a first signal transmitter which transmits the mixture signal via a communication channel, (a4) a first signal receiver which receives, via the communication channel, a second sound signal representing a second voice of the medical worker directed to the at least one of the living body and the attendant person, and (a5) a first sound output device which converts the second sound signal back into the second voice of the medical worker and outputs the second voice so that the at least one of the living body and the attendant person hears the second voice; and (B) a second signal transmitting and receiving device which is adapted to be disposed on a side of the medical worker, and includes (b1) a second signal receiver which receives the mixture signal via the communication channel from (a3) the first signal transmitter, (b2) a signal separator which separates the mixture signal back into the physical information signal and the first sound signal, (b3) a physical-information output device which outputs the physical information represented by the physical information signal so that the medical worker receives the physical information, (b4) a second sound generator which converts the first sound signal back into the first voice of the at least one of the living body and the attendant person and outputs the first voice so that the medical worker hears the first voice, (b5) a second sound detector which detects the second voice of the medical worker and generates the second sound signal representing the detected second voice, and (b6) a second signal transmitter which transmits the second sound signal via the communication channel to (a4) the first signal receiver.

In the medical communication system in accordance with the second aspect of the present invention, the transmission of voice of the medical worker and the transmission of voice of the living body and/or attendant person are effected in addition to the transmission of physical information of the living body, via the common communication channel. Thus, the medical worker can directly talk with the living body, and therefore can more accurately understand the condition of the living body.

According to a third aspect of the present invention, there is provided a medical communication system comprising: (A) a portable microsensor device which is adapted to be worn on a living body, and includes (a1) a physical information sensor which obtains physical information of the living body, and (a2) a first signal transmitter which transmits, at a first output power, a physical information signal representing the obtained physical information; (B) a monitor unit which is adapted to be disposed near to (A) the portable microsensor device, and includes (b1) a first signal receiver which receives the physical information signal from (a2) the first signal transmitter, and an instruction signal representing an instruction of a medical worker directed to the living body, (b2) abnormality identifying means for identifying whether the physical information represented by the physical information signal received by (b1) the first signal receiver is abnormal, (b3) a second signal transmitter which transmits, at a second output power higher than the first output power, the physical information signal identified as being abnormal by (b2) the abnormality identifying means, and (b4) an instruction output device which outputs the instruction represented by the instruction signal received by (b1) the first signal receiver; (C) a diagnosing and informing device which is adapted to be disposed away from (B) the monitor unit, and includes (c1) a second signal receiver which receives the physical information signal from (b3) the second signal transmitter, (c2) diagnosing means for diagnosing whether the physical information represented by the physical information signal received by (c1) the second signal receiver is abnormal, (c3) a wire communication circuit which transmits the physical information signal diagnosed as being abnormal by (c2) the diagnosing means, to the medical worker, via a wire communication line, and receives via the wire communication line the instruction signal representing the instruction of the medical worker in relation to the physical information represented by the physical information signal transmitted to the medical worker, and (c4) a third signal transmitter which transmits, to (b1) the first signal receiver, the instruction signal and a diagnosis signal representing that the physical information represented by the physical information signal received by (c1) the second signal receiver has been diagnosed as being abnormal by (c2) the diagnosing means, (B) the monitor unit further including (b5) an alarm device which issues an alarm indicating that the physical information represented by the physical information signal has been diagnosed as being abnormal by (c2) the diagnosing means, when (b1) the first signal receiver receives the diagnosis signal from (c4) the third signal transmitter.

In the medical communication system in accordance with the third aspect of the present invention, the monitor unit disposed near to the portable microsensor device transmits, to the diagnosing and informing device disposed away from the monitor unit, the physical information signal at an output power higher than that at which the microsensor device transmits the physical information signal. Thus, the rage of transmission of the physical information signal in the present system is broader than that in a conventional medical communication device disclosed in Unexamined Japanese Patent (JP) Application laid open under Publication No. 59(1984)-77760 which device does not employ any element corresponding to the monitor unit. In addition, even if the abnormality identifying means of the monitor unit identifies an abnormality of the physical information signal, the diagnosing and informing device does not transmit the physical information signal to the medical worker unless the diagnosing means diagnoses an abnormality of the physical information signal. In the event that the abnormality of physical information signal identified by the monitor unit is just a passing one or results from noise, unnecessary transmission of the physical information signal to the medical worker is effectively avoided. JP 59(1984)-77760 does not disclose any element corresponding to the diagnosing means. Furthermore, the signal transmitter of the portable microsensor device outputs the physical information signal at a low power and thus enjoys a small size. Since the abnormality identifying means, alarm device, and instruction output device are incorporated into the monitor unit, the size and weight of the microsensor device adapted to be worn on the living body are reduced, and accordingly the discomfort of the living body due to the wearing of the microsensor device is reduced. Unlike the microsensor device, the monitor unit is not necessarily worn on the living body. Even though the monitor unit may be worn on the living body, the location of wearing of the monitor unit on the living body can freely be selected. Therefore, the wearing of the monitor unit on the living body does not lead to increasing the discomfort of the living body.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
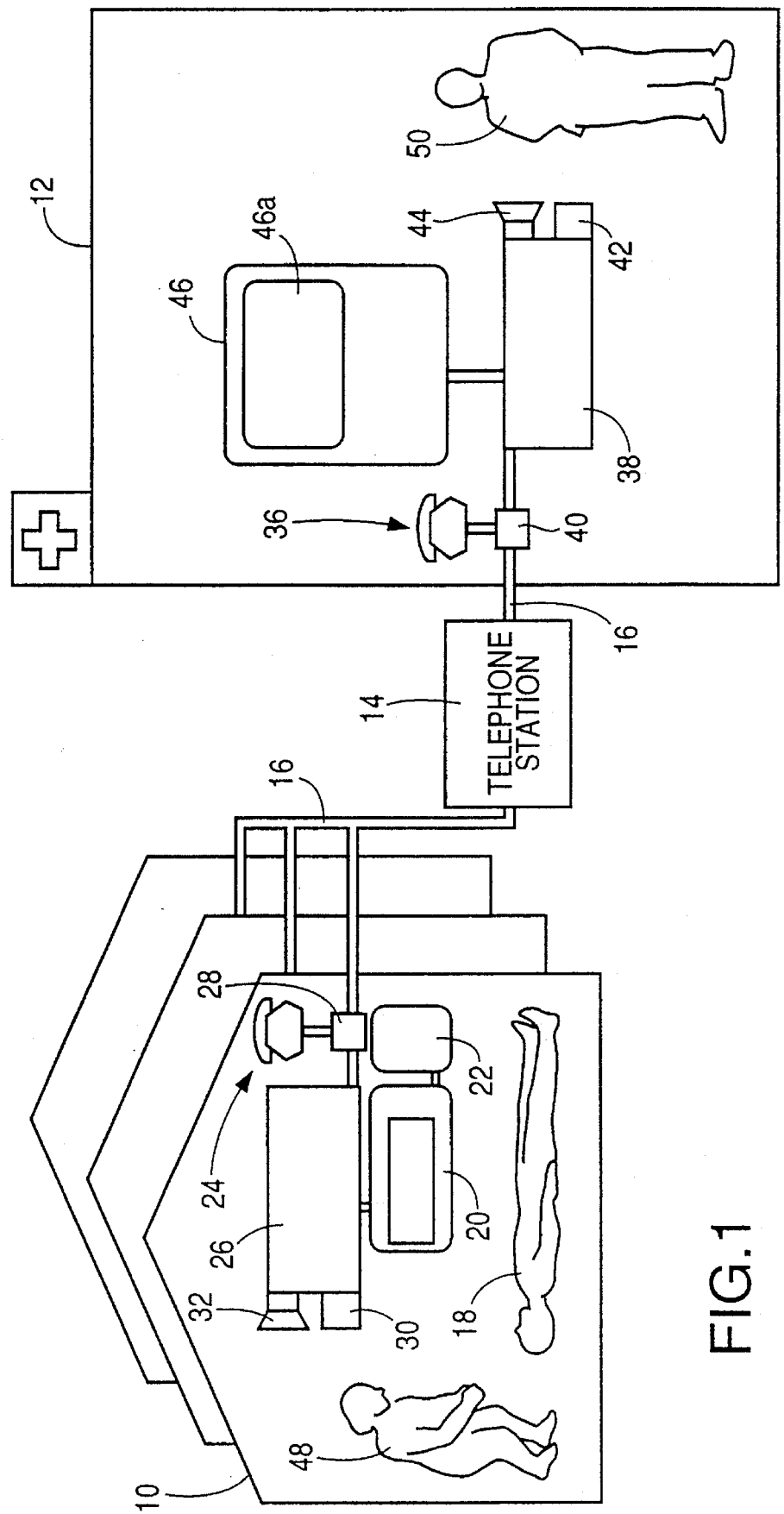
FIG. 1 is an illustrative view of a medical communication system embodying the present invention.

Referring to FIG. 1, there is shown a medical communication system embodying the present invention. In the figure, reference numeral 10 designates a plurality of houses or homes each of which is connected via a telephone line 16 and a telephone station 14 to a hospital 12.

In each home 10, there is disposed an electrocardiogram (ECG) monitor 20 including a plurality of electrodes (not shown) which are adapted to be worn on a patient 18 as a living body so as to obtain the ECG of the patient 18 as physical information of a living body. A recorder 22 is connected to the ECG monitor 20, and records the obtained ECG waveform. Thus, the ECG monitor 20 corresponds to a physical information sensor device for obtaining physical information of a living body.

In each home 10, there are also disposed a first telephone set 24 and a first transmitter-receiver (T-R) 26. Either one of the first telephone 24 and the first T-R 26 is connected to the telephone line 16, according to a current switching position of a first switching device (e.g., network control unit, NCU) 28. The first switch 28 is usually placed in a first switching position where the first telephone 24 is connected to the telephone line 16 and, when the first switch 28 is receiving a signal from the first T-R 26 or a second transmitter-receiver (T-R) 38 of the hospital 12, the first switch 28 is automatically switched from the first position to a second position where the first T-R 26 is connected to the telephone line 16 in place of the first telephone 24. The first T-R 26 includes a first microphone 30 and a first speaker 32, and is connected to the ECG monitor 20.

In the hospital 12, there are disposed a second telephone set 36 as well as the second T-R 38. Either one of the second telephone 36 and the second T-R 38 is connected to the telephone line 16, according to a current switching position of a second switching device 40 (e.g., NCU). The second switch 40 is usually placed in a first switching position where the second telephone 36 is connected to the telephone line 16 and, when the second switch 40 is receiving a signal from the second T-R 38 or the first T-R 26 of each home 10, the second switch 40 is automatically switched from the first position to a second position where the second T-R 38 is connected to the telephone line 16 in place of the second telephone 36. The second T-R 38 includes a second microphone 42 and a second speaker 44, and is connected to a host monitor device 46.

In FIG. 1, reference numeral 48 designates an attendant person (e.g., nurse) attending to the patient 18, and reference numeral 50 designates a doctor as a medical worker.

Figure 2:
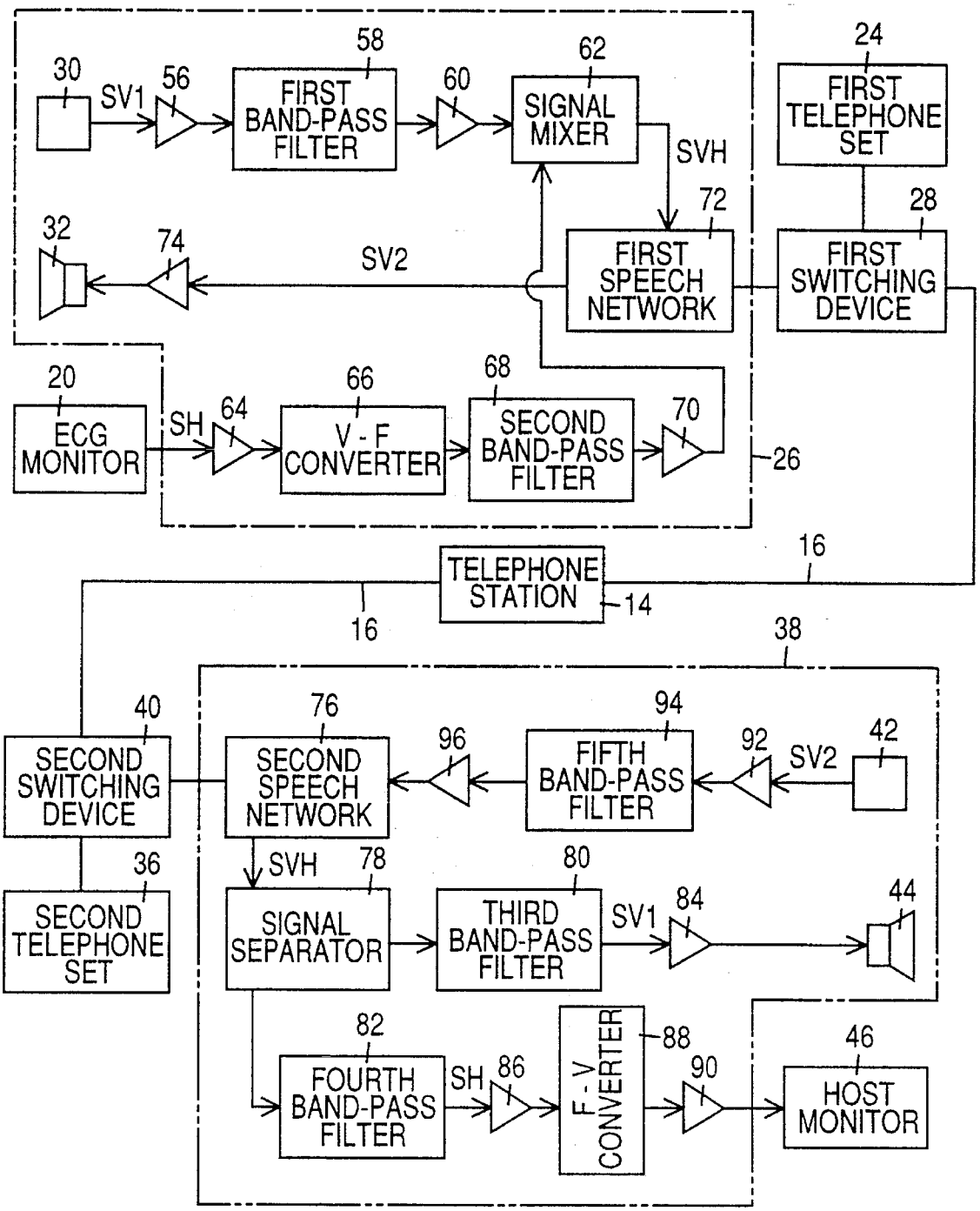
FIG. 2 is a diagrammatic view of an electric arrangement of the medical communication system of FIG. 1.

Hereinafter, there will be described the construction of the first and second T-Rs 26, 28 and the operation of the medical communication system including the two T-Rs 26, 28. In FIG. 2, the first T-R 26 is enclosed by a one-dot chain line and the second T-R 38 is enclosed by a two-dot chain line.

The first microphone 30 of the first T-R 26 detects voice of the patient 18 or the attendant 48, generates a sound signal, SV1, representing the detected voice, and supplies the signal SV1 to a first band-pass filter 58 via a limiting amplifier 56. The first band-pass filter 58 permits only a 0.3 kHz to 2.1 kHz frequency component of the sound signal SV1 to pass therethrough, thereby supplying the filtered signal SV1 to a signal mixer 62 via an amplifier 60.

Meanwhile, the ECG monitor 20 includes an electrocardiograph (not shown) which obtains the ECG waveform of the patient 18 through electrodes (not shown) worn on the patient 18, generates an ECG signal, SH, representing the obtained ECG waveform, and supplies the signal SH to a voltage-frequency (V-F) converter 66 via an amplifier 64. The V-F converter 66 modulates the ECG signal SH at a frequency higher than the frequency band (0.3–2.1 kHz) of the first band-pass filter 58, and supplies the modulated signal SH to a second band-pass filter 68. The second band-pass filter 68 permits only a 2.5 kHz to 3.0 kHz frequency component of the signal SH to pass therethrough, thereby supplying the filtered signal SH to the signal mixer 62 via an amplifier 70.

The signal mixer 62 mixes the sound signal SV1 and the ECG signal SH which have different frequencies, and supplies the thus obtained mixture signal, SVH, to a first speech network 72. The first speech network 72 is connected to the telephone line 16 via the first switching device 28 on one hand and is connected to the first speaker 32 via an amplifier 74 on the other hand. The first speech network 72 deals with the mixture signal SVH and a sound signal, SV2, received from the second T-R 38 at the hospital 12, in such a manner that the two signals SVH, SV2 are not mixed with each other. The mixture signal SVH includes the sound signal SV1 representing the voice of the patient 18 and/or attendant 48 directed to the doctor 50 at the hospital 12, and the sound signal SV2 represents voice of the doctor 50 directed to the patient 18 and/or attendant 48. Owing to the first speech network 72, the voice of the patient 18 and/or attendant 48 is transmitted to the doctor 50, and the voice of the doctor 50 is transmitted to the patient 18 and/or attendant 48, without any confusion.

The mixture signal SVH supplied to the first speech network 72 is transmitted via the first switching device 28, telephone line 16, and telephone station 14 to the hospital 12, i.e., a second speech network 76 via the second switching device 40 of the second T-R 38. With the second speech network 76, the voice of the doctor 50 is transmitted to the patient 18 and/or attendant 48, and the voice of the patient 18 and/or attendant 48 is transmitted to the doctor 50, without any confusion. The mixture signal SVH received at the second speech network 76 is supplied to a signal separator 78 which separates, using a reference frequency, the mixture signal SVH into a first component having frequencies lower than the reference frequency and including the sound signal SV1 and a second component having frequencies higher than the reference frequency and including the ECG signal SH, and supplies the first component including the sound signal SV1 to a third band-pass filter 80 and the second component including the ECG signal SH to a fourth band-pass filter 82.

The third band-pass filter 80 has the same frequency band (0.3–2.1 kHz) as that of the first band-pass filter 58 of the first T-R 26, and supplies the filtered sound signal SV1 to the second speaker 44 via an amplifier 4. The second speaker 44 converts the sound signal SV1 back into the voice of the patient 18 and/or attendant 48, and outputs the voice so that the doctor 50 hears the voice. The fourth band-pass filter 82 has the same frequency band (2.5–3.0 kHz) as that of the second band-pass filter 68 of the first T-R 26, and supplies the filtered ECG signal SH to a frequency-voltage (F-V) converter 88 via an amplifier 86. The F-V converter 88 demodulates the ECG signal SH modulated by the V-F converter 66 of the first T-R 26, and supplies the demodulated ECG signal SH to the host monitor device 46 via a direct-current amplifier 90. The host monitor 46 displays, on an image display 46a, the ECG waveform represented by the ECG signal SH.

The second microphone 42 detects voice of the doctor 50, and supplies a sound signal, SV2, representing the detected voice to a fifth band-pass filter 94 via a limiting amplifier 92. The fifth band-pass filter 94 permits only a 0.3 kHz to 3.0 kHz frequency component of the signal SV2 to pass therethrough, thereby supplying the filtered signal SV2 to the second speech network 76 via an amplifier 96. The sound signal SV2 supplied to the second speech network 76 is transmitted via the second switching device 40, telephone line 16, telephone station 14, first switching device 28, first speech network 72, and amplifier 74, to the first speaker 32 of the first T-R 26 of each home 10. The first speaker 32 converts the sound signal SV2 back into the voice of the doctor 50 and outputs the voice so that the patient 18 and/or attendant 48 hear the voice.

In the present embodiment, the first transmitter-receiver (T-R) 26 corresponds to a first signal transmitting and receiving device; the first speech network 72 corresponds to a first signal transmitter and a first signal receiver; and the first speaker 32 corresponds to an instruction output device. The second transmitter-receiver (T-R) 38 and the host monitor device 46 correspond to a second signal transmitting and receiving device; the second speech network 76 corresponds to a second signal transmitter and a second signal receiver; the host monitor device 46 corresponds to a physical-information output device; and the second microphone 42 corresponds to an instruction input device.

It emerges from the foregoing description that in the present embodiment, the signal mixer 62 mixes the sound signal SV1 supplied from the first microphone 30 disposed on the side of the patient 18 and/or attendant 48, and the ECG signal SH supplied from the ECG monitor device 20, into the mixture signal SVH, and the first speech network 72 receives the mixture signal SVH from the signal mixer 62 and transmits the mixture signal SVH via the telephone line 16, so that the second speech network 76 of the second T-R 38 at the hospital 12 receives the mixture signal SVH and the separator 78 separates the mixture signal SVH into the first component including the sound signal SV1 and the second component including the ECG signal SH. The sound signal SV1 passing through the third band-pass filter 80 is supplied to the second speaker 44 so that the voice of the patient 18 and/or attendant 48 is heard by the doctor 50, and simultaneously the ECG signal SH passing through the fourth band-pass filter 82 is supplied to the host monitor device 46 so that the ECG waveform of the patient 18 obtained by the ECG monitor 20 is displayed before the doctor 50 at the hospital 12. Meanwhile, if the sound signal SV2 supplied from the second microphone 42 disposed on the side of the doctor 50 is supplied to the second speech network 76 and the second speech network 76 transmits the sound signal SV2 via the telephone line 16, the sound signal SV2 is received at the first speech network 72 of the first T-R 26 on the side of the patient 18 and then the sound signal SV2 is supplied to the first speaker 32 so that the voice of the doctor 50 is heard by the patient 18 and/or attendant 48. With the present medical communication system, both the transmission of the ECG waveform of the patient 18 to the doctor 50 and the bidirectional transmissions of voices between the patient 18 and/or attendant 48 and the doctor 50 are concurrently effected via the single telephone line 16. Even though the doctor 50 may be at the hospital 12 distant from the patient 18 at his or her home 10, the doctor 50 can observe the patient's ECG waveform on the host monitor 46 and directly talk with the patient 18 and/or attendant 48, so that the doctor 50 can accurately grasp the current condition of the patient 18. In case of emergency, the doctor 50 can give instructions to the patient 18 and/or attendant 48 to take provisional medical treatments for the patient 18.

While in the first embodiment the ECG waveform of the patient 18 is obtained as physical information of a living body, it is possible to obtain, in place of, or in addition to, the ECG waveform, one or more sorts of physical information such as blood pressure, pulse rate, body temperature, blood oxygen saturation, and blood sugar of the patient 18.

Although the first embodiment relates to the case where the ECG monitor 20 and the first T-R 26 are disposed for monitoring each patient 18 at his or her home 10, it is possible to dispose the same elements 20, 26 for periodic physical checkup of business persons at their office. In the latter case, the present communication system connects the business office and the hospital 12. Otherwise, the medical communication system may be used to connect an ambulance car and the hospital 12 by radio communication. In the last case, an ambulance person corresponds to the attendant person 48.

In the first embodiment, the first speech network 72 serves as both the first signal transmitter and receiver and the second speech network 76 serves as both the second signal transmitter and receiver. However, in the case where radio communication is utilized as the common communication channel, the first signal transmitter and receiver may be provided as two independent elements, respectively, and similarly the second signal transmitter and receiver may be provided as two independent elements, respectively.

In the first embodiment, the signal separator 78 may be omitted and the third and fourth band-pass filters 80, 82 may be adapted to serve as the signal separator.

In the first embodiment, the signal mixer 62 is designed to simply mix the sound signal SV1 and the ECG signal SH which have difference frequencies, and the signal separator 78 is designed to simply separate the mixture signal SVH by using a reference frequency as a border between the sound signal SV1 and the ECG signal SH. However, the signal mixer may otherwise be designed to time-compress the signals SV1, SH and multiplex by time sharing the time-compressed signals into a multiplexed mixture signal SVH, and the signal separator may be designed to demultiplex the multiplexed mixture signal SVH back into the time-compressed signals SV1, SH and time-extend the time-compressed signals SV1, SH back into the original signals SV1, SH.

The first T-R 26 may be provided with an emergency switch (not shown) available for transmitting an emergency call to the doctor 50. The present communication system may be adapted such that, when the emergency switch is operated by the patient 18 or attendant 48, the first T-R 26 automatically transmits the ECG waveform of the patient 18 to the doctor 50 in addition to the emergency call.

A medical worker who receives, at the hospital 12, the

ECG waveform of each patient 18 from his or her home 10 and the voice of the patient 18 and/or attendant 48 may be different from the doctor 50, for example, may be a nurse.

Figure 3:
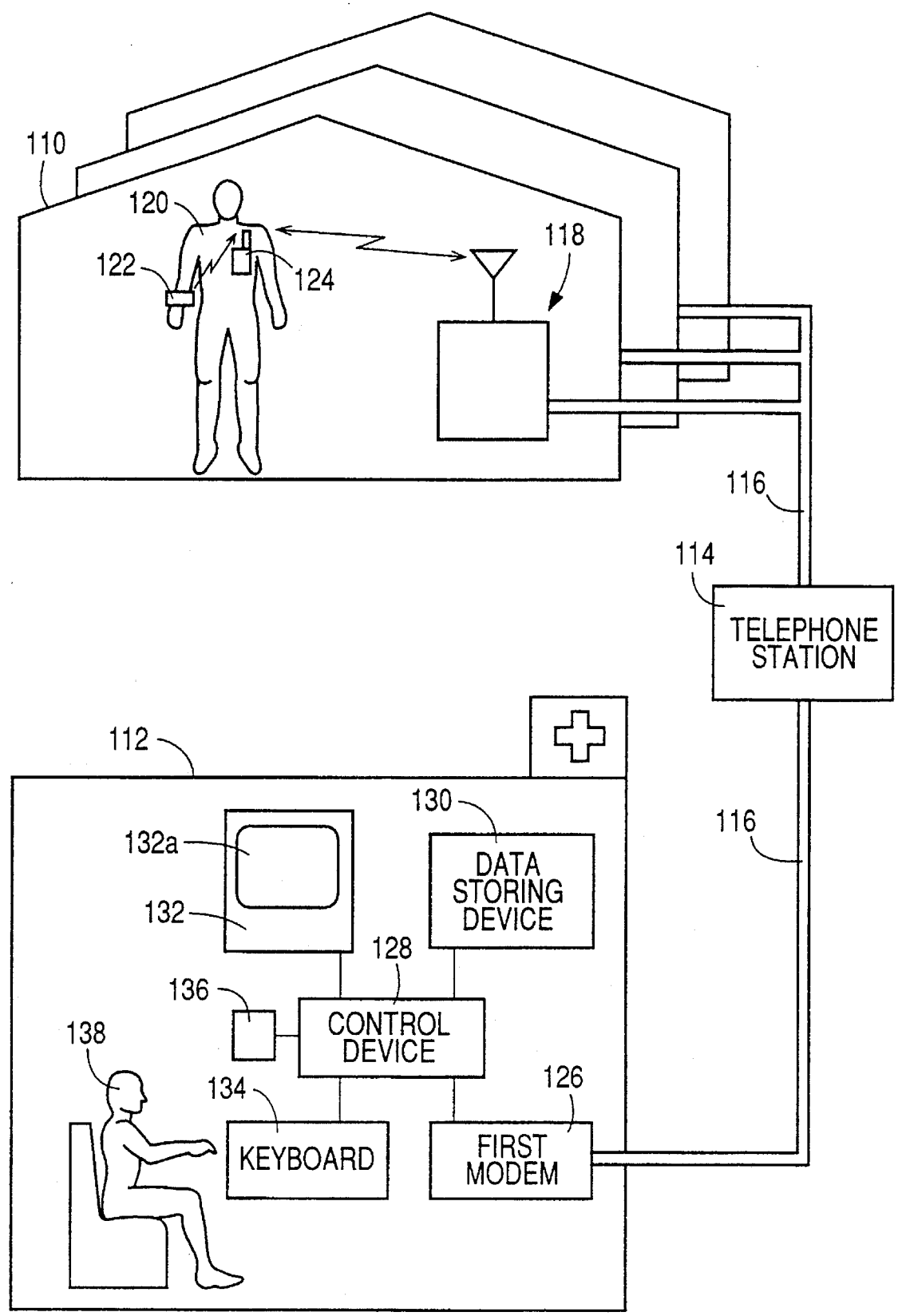
FIG. 3 is an illustrative view corresponding to FIG. 1, showing a medical communication system as a second embodiment of the present invention.

Referring next to FIGS. 3 through 9, there is shown a second embodiment of the present invention. The second embodiment also relates to a medical communication system. In FIG. 3, reference numeral 110 designates a plurality of houses or homes each of which is connected via a telephone line 116 and a telephone station 114 to a hospital 112.

In each home 110, there is disposed a diagnosing and informing device (hereinafter, abbreviated to "D-I" device) 118 which is connected to the telephone line 116. A watch-type microsensor device 122 is worn on a wrist of a patient 120 as a living body who may move away from the D-I device 118 disposed in the home 110. In addition, a monitor unit 124 is worn on a chest of the patient 120.

In the hospital 112, there is disposed a control device 128 which is connected to the telephone line 116 via a modem 126. The control device 128 is also connected to a data storing device 130, a host monitor device 132, a keyboard 134, and a microphone 136. The data storing device 130 stores various sorts of data of individual patients 120 in a magnetic recording medium such as a floppy disk. The host monitor 132 includes an image display 132a. In FIG. 3, reference numeral 138 designates a doctor as a medical worker.

Figure 4:
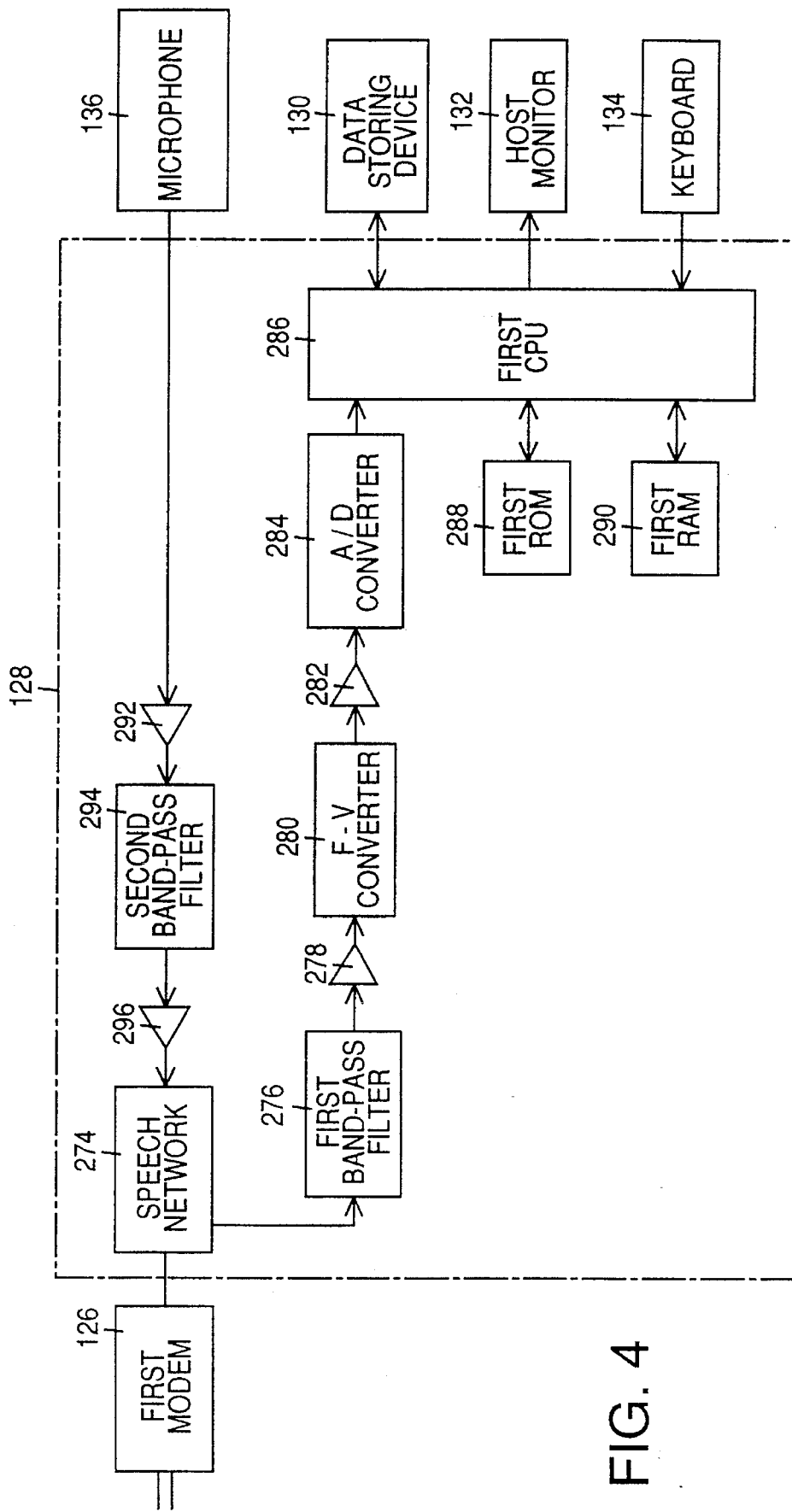
FIG. 4 is a diagrammatic view of an electric arrangement of a control device of the system of FIG. 3 disposed at a hospital 112.

FIG. 4 shows an electric arrangement of the control device 128. The D-I device 118 disposed at each home 110 is connected via the telephone line 116 to the hospital 112. Signals supplied from the D-I device 118 via the telephone line 116 are received by a speech network 274 via the first modem 126 and then supplied to a first band-pass filter 276. The first band-pass filter 276 supplies the filtered signals to a frequency-voltage (F-V) converter 280 via an amplifier 278. The F-V converter 280 supplies the demodulated signals to a first central processing unit (CPU) 286 via an amplifier 282 and an analog to digital (A/D) converter 284. The first CPU 286 processes input signals according to control programs pre-stored in a first read only memory (ROM) 288 by utilizing a temporary-storage function of a first random access memory (RAM) 290. The microphone 136 detects voice of the doctor 138, and supplies a sound signal representing the detected voice to a second band-pass filter 294 via a limiting amplifier 292. The band-pass filter 94 supplies the filtered signal to the speech network 274 via an amplifier 296. The sound signal supplied to the speech network 274 is transmitted via the first modem 126 and telephone line 116 to the D-I device 118 of each home 110.

Figure 5:
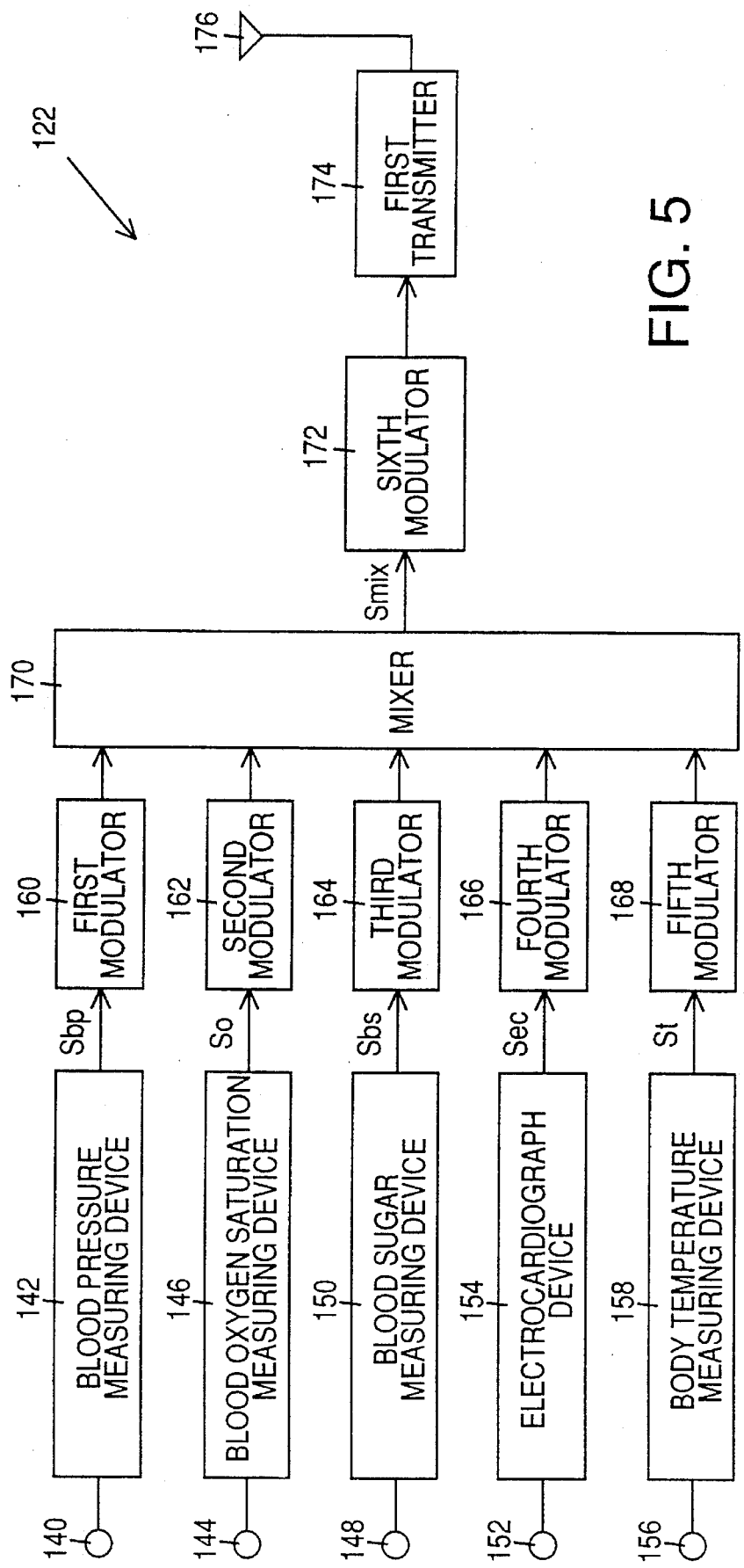
FIG. 5 is a diagrammatic view of an electric arrangement of a portable microsensor device of the system of FIG. 3 adapted to be worn on a patient 120 at his or her home 110.

FIG. 5 shows an electric arrangement of the portable microsensor device 122. The microsensor device 122 includes (a) a blood pressure measuring device 142, as disclosed in U.S. Pat. No. 4,269,193, which determines a systolic and a diastolic blood pressure of the patient 120 based on each of successive pulses of a pressure pulse wave signal produced by a pressure sensor 140 externally pressed on a radial artery of a wrist of the patient 120; (b) a blood oxygen saturation measuring device 146 which determines a blood oxygen saturation of the patient 120 based on photoelectric pulse wave signals produced by an oximeter probe 144 including two sorts of light emitting elements emitting respective lights having different wavelengths toward the skin of the patient 120 and a light receiving element detecting the respective lights reflected from the patient's skin; (c) a blood sugar measuring device 150 which determines a blood sugar of the patient 120 based on an output signal produced by a probe 148 including a pair of electrodes each of which is covered with a glucose-oxidase film and is held in contact with body fluid exuded by sucking the skin of the patient 120; (d) an electrocardiograph 154 which obtains an electrocardiogram of the patient 120 based on respective output signals produced by a plurality of electrodes 152 (only one 152 is shown in FIG. 4) held in contact with the skin of the patient 120; and (e) a body temperature measuring device 158 which determines a body temperature of the patient 120 based on an output signal produced by a thermistor 156 held in contact with the skin of the subject 120.

In the second embodiment, each of the sensor devices 142, 146, 150, 154, and 158 corresponds to a physical information sensor device, and each of the blood pressure, blood oxygen saturation, blood sugar, electrocardiogram, and body temperature corresponds to physical information of a living body.

The blood pressure measuring device 142 produces a blood pressure signal, Sbp, which is supplied to a mixer 170 via a first modulator 160; the blood oxygen saturation measuring device 146 produces a blood oxygen saturation signal, So, which is supplied to the mixer 170 via a second modulator 162; the blood sugar measuring device 150 produces a blood sugar signal, Sbs, which is supplied to the mixer 170 via a third modulator 164; the electrocardiograph 154 produces an electrocardiogram signal, Sec, which is supplied to the mixer 170 via a fourth modulator 166; and the body temperature measuring device 158 produces a body temperature signal, St, which is supplied to the mixer 170 via a fifth modulator 168. The mixer 170 mixes the five signals Sbp, So, Sbs, Sec, St with each other, and produces a mixture signal, Smix, which is modulated at a predetermined frequency by a sixth modulator 172 and subsequently is transmitted by radio from a first antenna 176 of a first transmitter 174. The first transmitter 174 transmits the mixture signal Smix at a low output power in terms of a signal transmission range of about 10 m.

Figure 6:
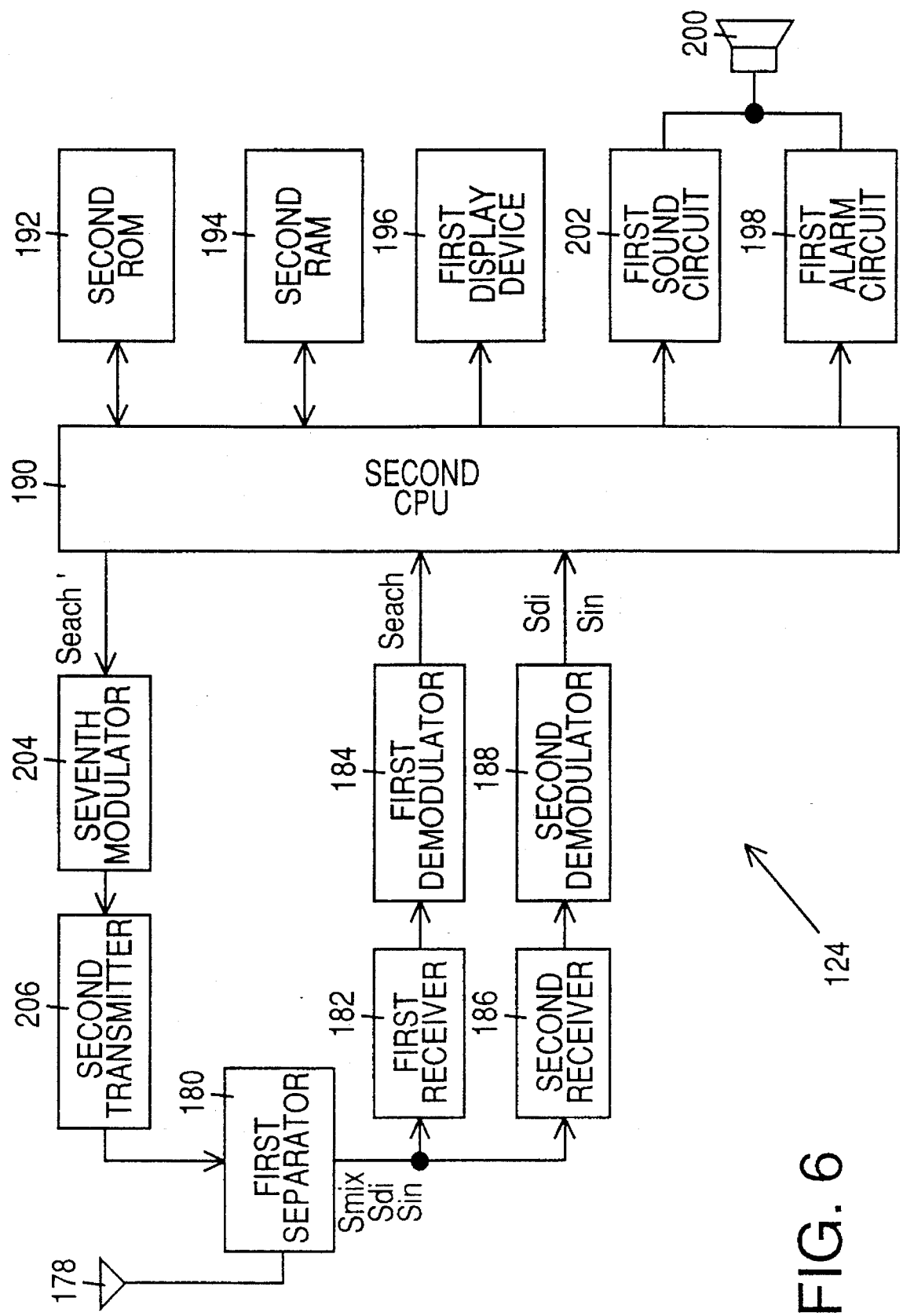
FIG. 6 is a diagrammatic view of an electric arrangement of a monitor unit of the system of FIG. 3.

FIG. 6 shows an electric arrangement of the monitor unit 124. The monitor unit 124 includes a second antenna 178 which receives the mixture signal Smix from the portable microsensor device 122, a diagnosis signal, Sdi, (described later) from the D-I device 118, and an instruction signal, Sin, (described later) from the D-I device 118. The received signals Smix, Sdi, Sin are supplied to a first separator 180 which supplies the signal Smix to a first demodulator 184 via a first receiver 182 and supplies the signals Sdi, Sin to a second demodulator 188 via a second receiver 186. The first demodulator 184 demodulates the modulation of the mixture signal Smix by the sixth modulator 172 of the microsensor device 122, and demodulates the respective modulations of the mixture signal Smix by the first to fifth modulators 160 to 168. The first demodulator 184 supplies each of the demodulated signals Sbp, So, Sbs, Sec, and St (hereinafter, referred to as "each sensor signal, Seach") to a second CPU 190. The second demodulator 188 demodulates the modulation of the signals Sdi, Sin by an eighth modulator 132 (described later) of the D-I device 118, and supplies the demodulated signals Sdi, Sin to the second CPU 190.

The second CPU 190 processes input signals according to control programs pre-stored in a second ROM 192 by utilizing a temporary-storage function of a second RAM 194. More specifically, the second CPU 190 controls a first display device 196 to display the physical information represented by each sensor signal Seach as an input to the CPU 190. In addition, the second CPU 190 identifies an abnormality of each sensor signal Seach and controls the first display 196 to blink an indication (e.g., predetermined message) indicating that an abnormality of each sensor signal Seach has been identified. When the diagnosis signal Sdi is supplied to the second CPU 190, the CPU 190 drives a first alarm circuit 198 to operate a first speaker 200 to issue an alarm sound, and simultaneously the CPU 190 operates the first display 196 to display a diagnosis (e.g., low blood pressure) represented by the diagnosis signal Sdi. Furthermore, when the instruction signal Sin is supplied to the second CPU 190, the CPU 190 drives a first sound circuit 202 to operate the first speaker 200 to issue a voice, i.e., instructions of the doctor 138 represented by the signal Sin. In the second embodiment, the first sound circuit 202 and the first speaker 200 cooperate with each other to provide an instruction output device.

The second CPU 190 supplies, according to a control program pre-stored in the second ROM 192, each sensor signal Seach for which an abnormality has been identified (hereinafter, referred to as the "abnormal signal Seach'"), to a seventh modulator 204. The abnormal signal Seach' is modulated at a predetermined frequency by the seventh modulator 204, and transmitted by the second antenna 178 via a second transmitter 206 and the first separator 180. The second transmitter 206 transmits the abnormal signal Seach' at an output power higher than that of the first transmitter 174 of the portable microsensor device 122, that is, transmits the signal Seach' within a signal transmission range of about 100 m.

Figure 7:
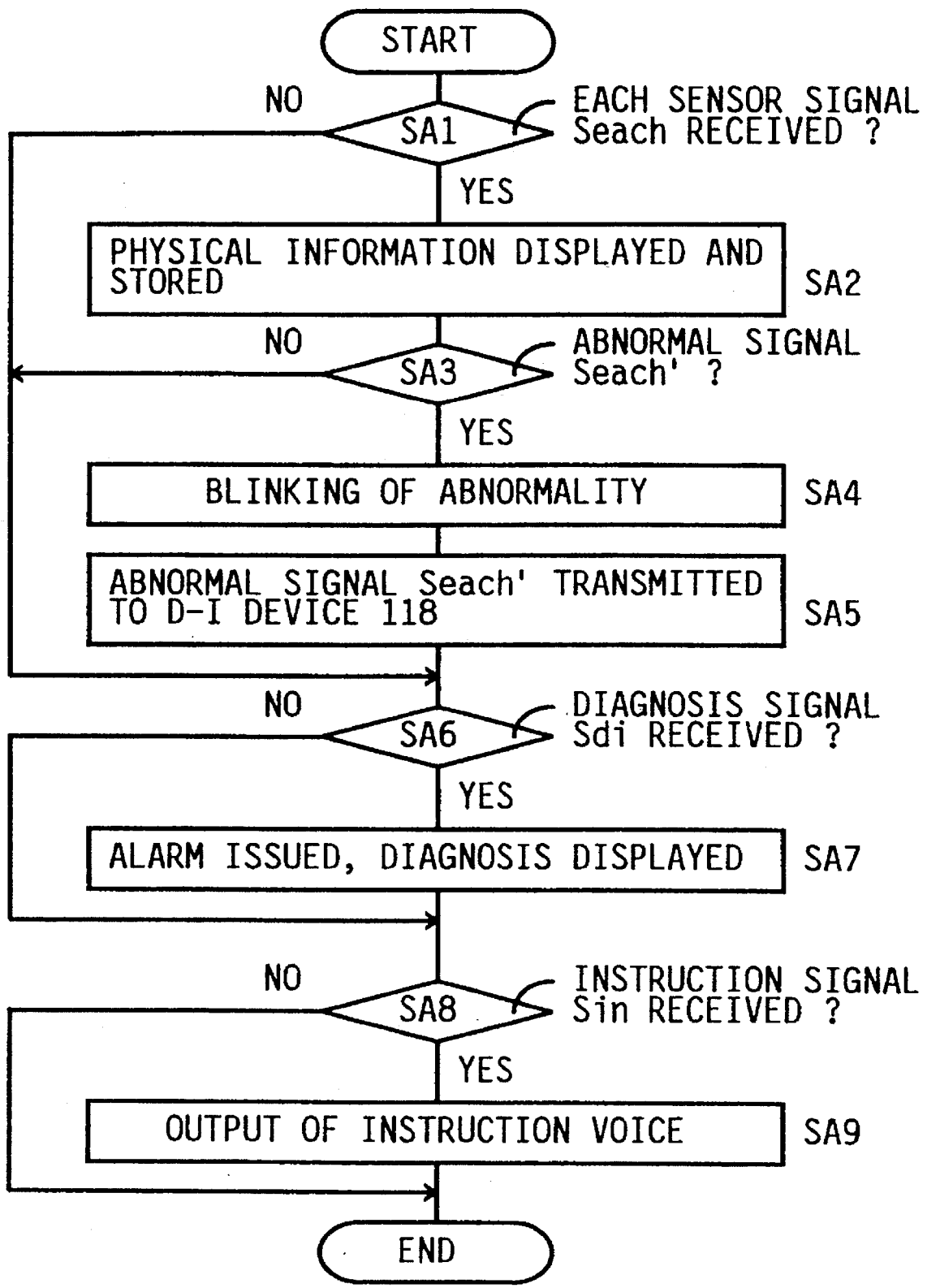
FIG. 7 is a flow chart representing a control program according to which the monitor unit of FIG. 6 operates.

FIG. 7 shows a flow chart representing a control program according to which the monitor unit 124 operates. First, at Step SA1, the second CPU 190 judges whether the CPU 190 has received each sensor signal Seach from the portable microsensor device 122. If a negative judgment is made at Step SA1, the control of the CPU 190 skips Steps SA2 to SA5 and proceeds with Step SA6. On the other hand, if a positive judgment is made at Step SA1, the control goes to Step SA2 to operate the first display 196 to display the physical information represented by each sensor signal Seach of the patient 120, i.e., each sort of physical information, and subsequently store the physical information in the second RAM 194. At the following Step SA3, the CPU 190 identifies whether the physical information represented by each sensor signal Seach is abnormal, by judging whether a value (e.g., blood pressure, pulse rate, etc.) of the physical information does not fall within a corresponding one of respective standard value ranges predetermined for the five sorts of physical information.

If a negative judgment is made at Step SA3, the control of the second CPU 190 skips Steps SA4 and SA5 and goes to Step SA6. On the other hand, if a positive judgment is made at Step SA3, the control goes to Step SA4 to operate the first display 196 to blink a predetermined indication indicating that an abnormality has been identified. Step SA 4 is followed by Step SA5 to read out the physical information stored in the RAM 194 for a predetermined time duration (e.g., one hour) before the identification of abnormality, and transmit the one-hour physical information to the D-I device 118 via the second antenna 178 (hereinafter, the one-hour physical information will be referred to simply as the abnormal signal Seach').

At the following Step SA6, the second CPU 190 judges whether the CPU 190 has received a diagnosis signal Sdi representing a diagnosis made by the D-I device 118, from a third antenna 208 of the D-I device 118. If a negative judgment is made at Step SA6, the control of the CPU 190 skips Step SA7 and goes to Step SA8. On the other hand, if a positive judgment is made at Step SA6, the control goes to Step SA7 to drive the first alarm circuit 198 to operate the first speaker 200 to issue an alarm sound indicating that an abnormality has been identified on the patient 120, and additionally to operate the first display 196 to display the diagnosis represented by the diagnosis signal Sdi. The diagnosis represented by the diagnosis signal Sdi indirectly indicates that the abnormal signal Seach' of the patient 120 transmitted to the D-I device 118 has been diagnosed as being abnormal by the D-I device 118 (described later).

At the following Step SA8, the second CPU 190 judges whether the CPU 190 has received an instruction signal Sin representing voice or instructions of the doctor 138 directed to the patient 120, from the third antenna 208 of the D-I device 118. If a negative judgment is made at Step SA8, the control of the CPU 190 skips Step SA9, and thus the current control cycle is ended. On the other hand, if a positive judgment is made at Step SA8, the control goes to Step SA9 to drive the first sound circuit 202 to operate the first speaker 200 to produce the instructive voice of the doctor 138 represented by the instruction signal Sin.

Figure 8:
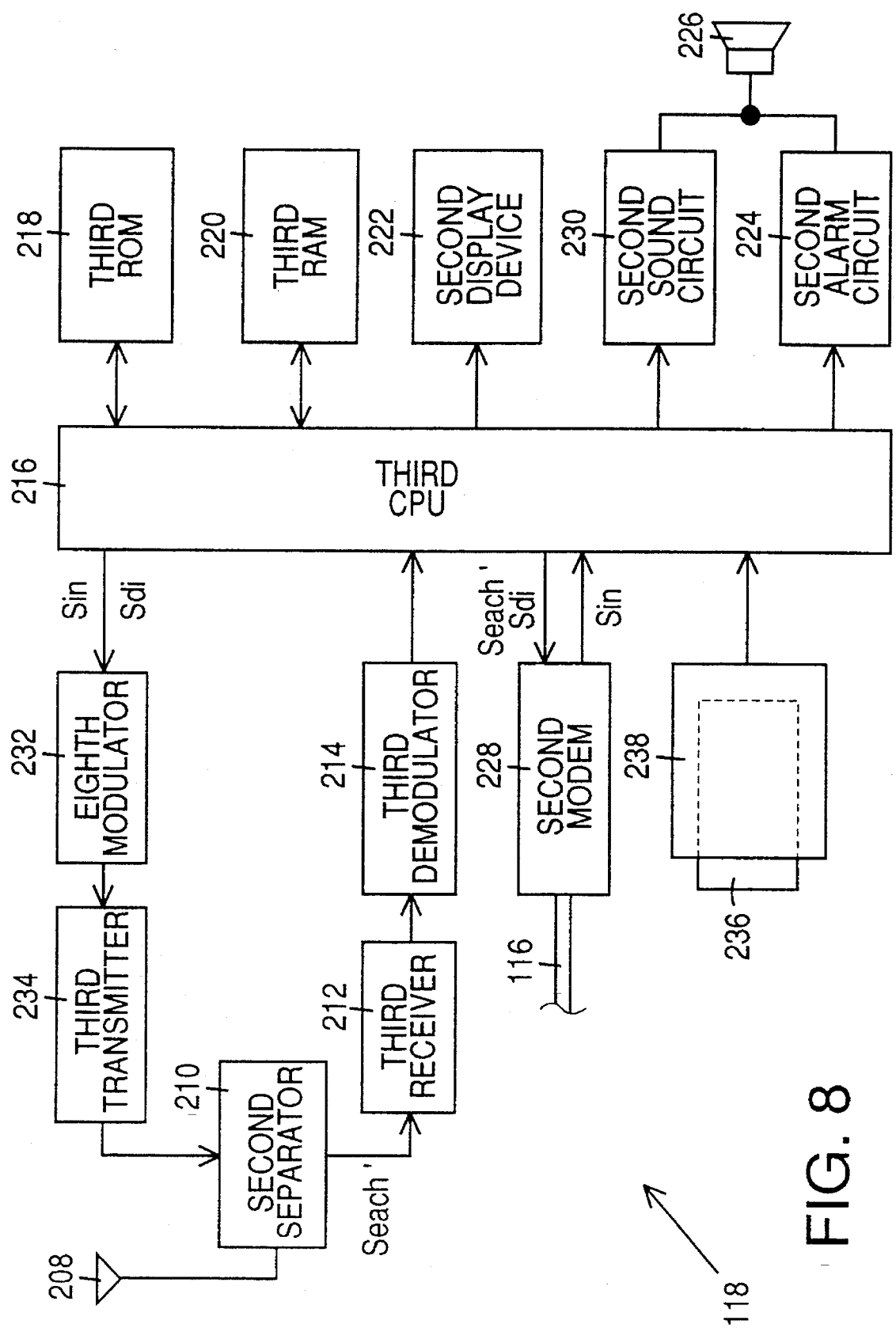
FIG. 8 is a diagrammatic view of an electric arrangement of a diagnosing and informing (D-I) device of the system of FIG. 3.

FIG. 8 shows an electric arrangement of the diagnosing and informing (D-I) device 118. As described above, the one-hour physical information stored before the identification of an abnormality of each sensor signal Seach, that is, abnormal signal Seach' is received by the third antenna 208 of the D-I device 118, and supplied to a third CPU 216 via a second separator 210, a third receiver 212, and a third demodulator 214.

The third CPU 216 processes input signals according to control programs pre-stored in a third ROM 220 by utilizing a temporary-storage function of a third RAM 220. The third CPU 216 controls a second display device 222 to display the physical information represented by the abnormal signal Seach' as an input to the CPU 216. In addition, the second CPU 216 controls the third display 222 to blink an indication indicating that an abnormality of each sensor signal Seach has been identified by the monitor unit 124. Furthermore, the third CPU 216 automatically makes a diagnosis based on the abnormal signal Seach' which has provisionally been identified as being abnormal by the monitor unit 124. When the third CPU 216 diagnoses the abnormal signal Seach' as being abnormal, for example, low blood pressure, the CPU 216 drives a second alarm circuit 224 to operate a second speaker 226 to issue an alarm sound. In addition, the CPU 216 supplies a diagnosis signal Sdi representing the thus made diagnosis, to the eighth modulator 232 which modulates the diagnosis signal Sdi. The modulated diagnosis signal Sdi is transmitted by the third antenna 208 via a third transmitter 234 and the second separator 210, so that the monitor unit 124 receives the diagnosis signal Sdi and splays the diagnosis represented by the signal Sdi. Furthermore, the third CPU 216 supplies the abnormal signal Seach' and the diagnosis signal Sdi to a second modem 228 via a digital to analog (D/A) converter and a speech network (not shown). Thus, the signals Seach', Sdi are transmitted to the hospital 112 via the telephone line 116.

When the third CPU 216 receives an instruction signal Sin representing voice or instructions of the doctor 138, via the telephone line 116 and the second modem 228, the CPU 216 drives, according to a control program pre-stored in the third ROM 218, a second sound circuit 230 to operate the second speaker 226 to output voice or instructions of the doctor 138 represented by the instruction signal Sin. In addition, the third CPU 216 supplies the instruction signal Sin to the eighth modulator 232 which modulates the instruction signal Sin. The modulated instruction signal Sin is transmitted by the third antenna 208 via the third transmitter 234 and the second separator 210, so that the monitor unit 124 receives the instruction signal Sin and outputs the instructive voice of the doctor 138 represented by the signal Sin. The instruction signal Sin is supplied from the second modem 228 to the third CPU 216 via the speech network and an A/D converter (not shown).

A card reading device 238 is connected to the third CPU 216. The card reader 238 reads an identification (ID) code and other data recorded on a memory card 236 being inserted in the card reader 238. The ID code of the memory card 236 identifies the patient 120. The ID code and other data read from the memory card 136 by the card reader 138 are transmitted with the abnormal signal Seach' and the diagnosis signal Sdi to the doctor 138 at the hospital 112 via the telephone line 116.

Figure 9:
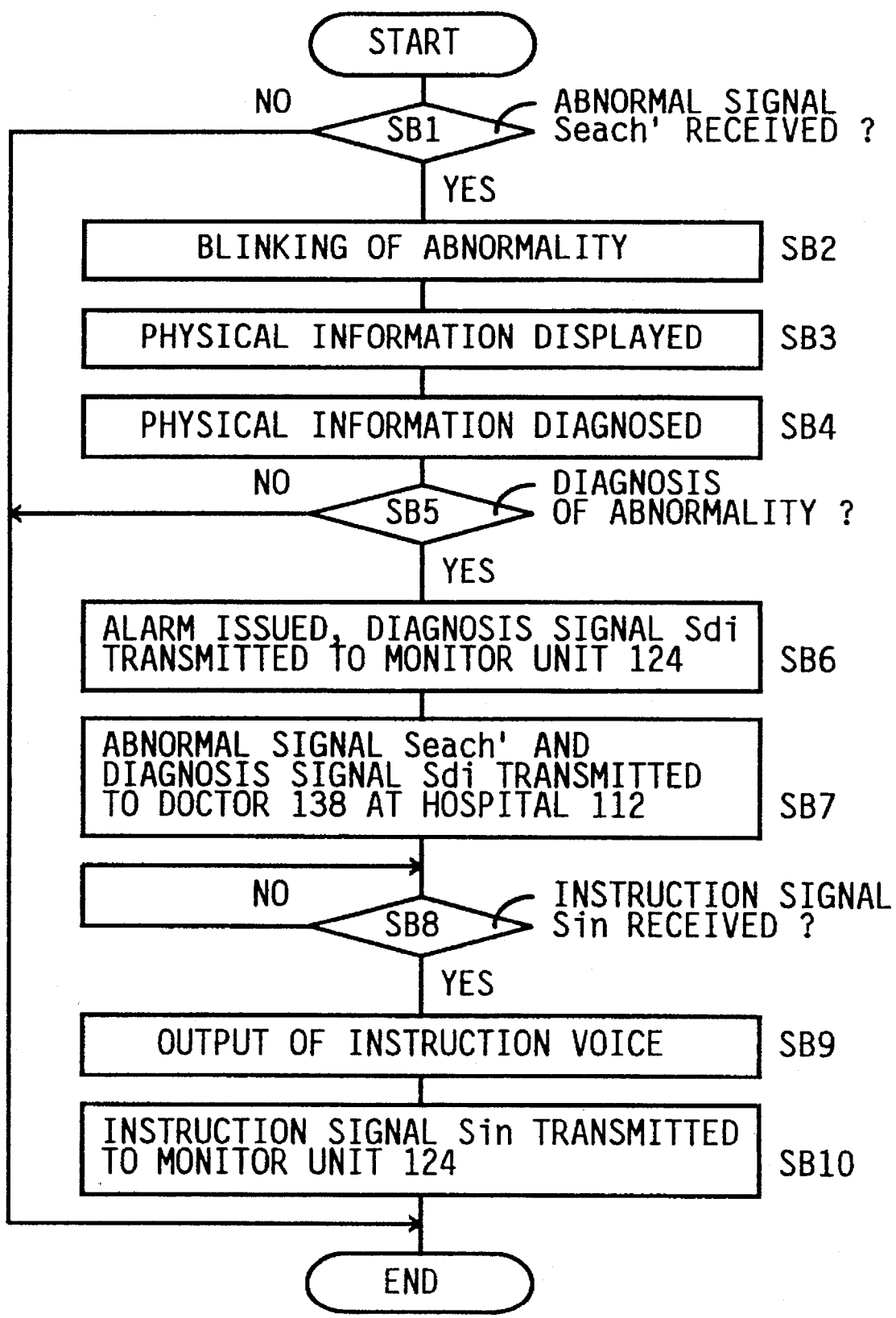
FIG. 9 is a flow chart representing a control program according to which the D-I device of FIG. 8 operates.

FIG. 9 shows a flow chart representing a control program according to which the D-I device 118 operates. First, at Step SB1, the third CPU 216 judges whether the CPU 216 has received the abnormal signal Seach' from the monitor unit 124. If a negative judgment is made at Step SB1, the current control cycle is ended. On the other hand, if a positive judgment is made at Step SB1, the control goes to Step SB2 to operate the second display 222 to blink an indication indicating that an abnormality has been identified by the monitor unit 124. At the following Step SB3, the CPU 216 operates the second display 222 to display the physical information represented by the abnormal signal Seach', that is, one-hour physical information stored before the identification of an abnormality of each sensor signal Seach).

Step SB3 is followed by Step SB4 to make a diagnosis (e.g., low blood pressure, high pulse rate, etc.) based on the physical information represented by the abnormal signal Seach', thereby removing the identification of a passing abnormality or the incorrect identification of an abnormality due to, e.g., noise mixed with each sensor signal Seach. This diagnosis may be made by judging whether the last value of the physical information falls within a value range determined based on an average of respective values of the physical information represented by the abnormal signal Seach'. Step SB4 is followed by Step SB5 to judge whether the abnormal signal Seach' has been diagnosed as being abnormal again at Step SB4. If a negative judgment is made at Step SB5, the current control cycle is ended. On the other hand, if a positive judgment is made at Step SB5, the control goes to Step SB6 to drive the alarm circuit 224 to operate the second speaker 226 to issue an alarm sound, and transmit the diagnosis signal Sdi representing the diagnosis made at Step SB4 to the monitor unit 124.

Step SB6 is followed by Step SB7 to transmit the abnormal signal Seach' and the diagnosis signal Sdi to the doctor 138 at the hospital 112 via the telephone line 116. At the following Step SB8, the third CPU 216 judges whether the CPU 216 has received an instruction signal Sin representing the voice or instructions of the doctor 138 directed to the patient 120, via the telephone line 116 and the second modem 228. If a negative judgment is made at Step SB8, the CPU 216 repeats Step SB8 and waits for a positive judgment being made at this step. On the other hand, if a positive judgment is made at Step SB8, the control goes to Step SB9 to drive the second sound circuit 230 to operate the second speaker 226 to produce the instructive voice of the doctor 138 represented by the instruction signal Sin. At the following Step SB10, the third CPU 216 supplies the instruction signal Sin to the monitor unit 124 so that the monitor unit 124 outputs the instructions of the doctor 138 toward the patient 120. When the control device 128 receives the abnormal signal Seach' and other signals via the telephone line 116 and the first modem 126, the control device 128 operates an alarm device (not shown) to issue an alarm sound, and the doctor 138 must give some instructions to the patient 120 in relation to the physical information represented by the abnormal signal Seach'. Thus, the control of the third CPU 216 can proceed from Step SB8 to Step SB9.

As described previously, the control device 128 disposed at the hospital 112 has a microcomputer including the CPU 286, ROM 288, and RAM 290, and operates the host monitor device 132 to display the physical information represented by the abnormal signal Seach' and the diagnosis made by the D-I device 118 and represented by the diagnosis signal Sdi. Thus, the doctor 138 can view, on the host monitor 132, both the abnormal physical information obtained during the predetermined time duration and the diagnosis made based on the abnormal physical information by the D-I device 118. The doctor 138 can make access, as needed, to the personal data of the patient 120 stored in the data storing device 130, by operating the keyboard 134, so that the doctor 138 can accurately understand the physical condition of the patient 120. The abnormal signal Seach' of the patient 120 is added to his or her personal data in the data storing device 130.

When the doctor 138 gives instructions for provisional medical treatments of the patient 120, the instructive voice is detected by the microphone 136 which converts the detected voice into an instruction signal Sin which is transmitted via the control device 128, first modem 126, and telephone line 116 to the second modem 128 of the D-I device 118, as shown in FIGS. 4 and 8. As a result, the instructive voice of the doctor 138 directed to the patient 120 is output from the second speaker 226 of the D-I device 118, and additionally the instruction signal Sin is transmitted from the D-I device 118 to the monitor unit 124 so that the instructions of the doctor 138 are output in his or her voice from the speaker 200 of the monitor unit 124.

In the second embodiment, the mixture signal Smix transmitted in the form of a radio wave from the first transmitter 174 of the portable microsensor device 122 worn on the patient 120, is considerably weak, because the output power of the first transmitter 174 is selected at a low level for the purpose of reducing the overall weight and size of the microsensor device 122. However, the weak signal Smix can be received by the monitor unit 124 worn on the patient 120 and disposed near to the microsensor device 122, and the second transmitter 206 of the monitor unit 124 transmits the abnormal signal Seach' at an output power higher than that of the first transmitter 174, to the D-I device 118 disposed away from the monitor unit 124. Thus, the microsensor device 122 cooperates with the monitor unit 124 to provide a wide range of transmission of the mixture signal Smix or abnormal signal Seach'.

In addition, in the second embodiment, even in the case where the monitor unit 124 identifies an abnormality of each sensor signal Seach, the D-I device 118 does not transmit the abnormal signal Seach' to the doctor 138 at the hospital 112, unless the D-I device 118 diagnoses the signal Seach' as being abnormal again. Thus, the present medical communication system effectively prevents the doctor 138 or hospital 112 from being unnecessarily informed of a passing or noise-induced abnormality of each sensor signal Seach identified by the monitor unit 124.

In the second embodiment, both the diagnosis made by the D-I device 118 and the physical information represented by the abnormal signal Seach' are displayed on the host monitor device 132 of the hospital 112. While the data displayed on the host monitor 132, the doctor 138 may make access, as needed, to the personal data of the patient 120 stored in the data storing device 130. Thus, the doctor 138 can accurately grasp the current condition of the patient 120. The present communication system allows the doctor 138 to give instructions to the patient 120 and/or an attendant person via the telephone line 116 through which the abnormal signal Seach' and diagnosis signal Sdi are transmitted to the doctor 138 from the D-I device 118. For example, in case of emergency, the doctor 138 can directly instruct the patient 120 or his or her attendant to take provisional medical treatments for the patient 120.

In the second embodiment, the first transmitter 174 of the portable microsensor device 122 outputs a weak signal. Meanwhile, the CPU 190, ROM 192, and RAM 194 of the monitor unit 124 functions as abnormality identifying means; the alarm circuit 198 and speaker 200 of the same 124 provides an alarm device; the sound circuit 202 and speaker 200 of the same 124 provides an instruction output device; and the monitor unit 124 further includes the display device 96. That is, the monitor unit 124 takes over, from the microsensor device 122, the abnormality identifying means, alarm device, instruction output device, and display device. Thus, the microsensor device 122 which is adapted to be worn on the patient 120 enjoys a small size and a light weight, so that the discomfort of the patient 120 due to the wearing of the microsensor device 122 is considerably reduced.

Although in the second embodiment the monitor unit 124 is worn on the patient 120, it is not required that the monitor unit 124 be always worn on the patient 120 like the microsensor device 122. In fact, the monitor unit 124 may be disposed near to the patient 120 within the signal transmission range of the transmitter 174 of the microsensor device 122. In the second embodiment, the location of wearing of the monitor unit 124 on the patient 120 can be selected more freely than the microsensor device 122, so that the discomfort of the patient 120 due to the wearing of the monitor unit 124 including the abnormality identifying means, alarm device, instruction output device, and display device is not increased so much.

In the second embodiment, even when the monitor unit 124 identifies an abnormality of each sensor signal Seach obtained from the patient 120, neither the monitor unit 124 nor the D-I device 118 issues an alarm sound unless the D-I device 118 again diagnoses the signal Seach' as being abnormal. In the event that the abnormality of each sensor signal Seach identified by the monitor unit 124 is a passing one or a noise-induced one, the unnecessary issuance of an alarm sound is effectively avoided.

Figure 10:
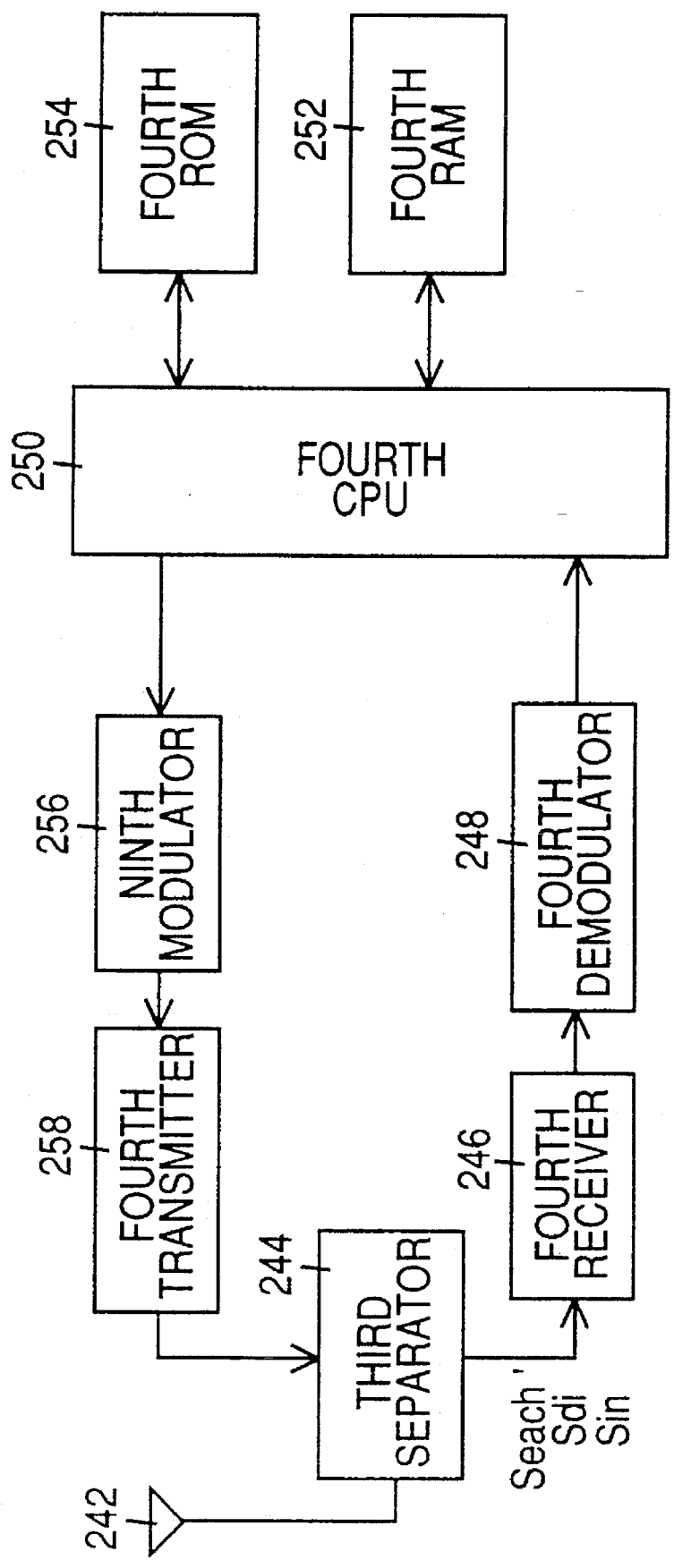
FIG. 10 is a diagrammatic view of an electric arrangement of a repeater disposed between a monitor unit and a D-I device of a medical communication system as a third embodiment of the present invention.

Hereinafter, there will be described a third embodiment of the present invention by reference to FIG. 10. FIG. 10 shows an electric arrangement of a repeater 240 which is disposed between a monitor unit and a D-I device (not shown) which are the same as the corresponding elements 124, 118 of the second embodiment. The repeater 240 includes a fourth antenna 242 which receives an abnormal signal Seach' from the monitor unit and receives a diagnosis signal Sdi and an instruction signal Sin from the D-I device. The signals Seach', Sdi, Sin are supplied to a fourth CPU 250 via a third separator 244, fourth receiver 246, and a fourth demodulator 248. The fourth CPU 250 processes the supplied signals Seach', Sdi, Sin according to control programs pre-stored in a fourth ROM 254 by utilizing a temporary-storage function of a fourth RAM 252, so that those signals are re-transmitted from the fourth antenna 242 without any confusion. The fourth CPU 250 supplies the signals Seach', Sdi, Sin to the fourth separator 244 via a ninth modulator 256 and a fourth transmitter 258. A plurality of repeaters 240 may be provided between the monitor unit and the D-I device, so that the transmission range of the abnormal signal Seach' may be broadened.

Although in the second embodiment the five sorts of physical information sensors, i.e., blood pressure sensor 142, blood oxygen saturation sensor 146, blood sugar sensor 150, electrocardiograph 154, and body temperature sensor 158 are employed, it is possible to employ only one of those sensors or otherwise employ one or more sensors different from those sensors.

While in the second embodiment not only the monitor unit 124 but also the D-I device 118 are adapted to issue an alarm sound indicating that each sensor signal Seach has been diagnosed as being abnormal, it is possible to adapt the D-I device 118 not to have this function.

While in the second embodiment the monitor unit 124 and the D-I device 118 are adapted to issue an alarm sound, it is possible to adapt each element 124, 118 to issue an alarm voice, or blink an alarm message on the display 196, 122 indicating that each sensor signal Seach has been diagnosed as being abnormal.

Although in the second embodiment the monitor unit 124 is adapted to output the instructions of the doctor 138 by way of vocal sound, it is possible to adapt the monitor unit 124 to output the doctor's instructions on the display device 196. In the latter case, the display device 196 corresponds to the instruction output device.

While in the second embodiment the monitor unit 124 and the D-I device 118 are adapted to blink, on the display 196, 122, an indication (e.g., message) indicating that each sensor signal Seach has been identified as being abnormal by the monitor unit 124, it is possible to adapt one or both of the monitor unit 124 and the D-I device 118 not to have this function, because the identification of abnormality of each sensor signal Seach by the monitor unit 124 is just a provisional one.

While in the second embodiment the display device 196 of the monitor unit 124 and the host monitor device 132 at the hospital 112 are adapted to display the abnormality diagnosis made by the D-I device 118, it is possible to adapt one or both of the monitor unit 124 and the host monitor 132 not to have this function, because the patient 120 and the doctor 138 are informed of the abnormality diagnosis by way of alarm sound.

In the second embodiment, the control device 128 disposed at the hospital 112 may be designed to operate an alarm device (e.g., speaker) to issue an alarm sound to the doctor 138, when the control device 128 receives the abnormal signal Seach' and diagnosis signal Sdi from each home 110 via the telephone line 116.

In the second embodiment, the D-I device 118 selects the abnormal signal Seach' identified as being abnormal by the monitor unit 124, from each sensor signal Seach corresponding to the five sorts of physical information, and transmits only the selected abnormal signal Seach' to the hospital 112. However, it is possible to adapt the D-I device 118 to transmit all sorts of sensor signals Seach including the abnormal signal Seach', to the hospital 112, upon identification of abnormality of each sensor signal Seach.

In the second embodiment, the patient 120 may walk out of the home 110 within the signal transmission and receiving range of the monitor unit 124 and D-I device 118. The D-I device 118 may be disposed at a place different from the patient's home 110, for example, at the patient's business office.

Although in the second embodiment the monitor unit 124 employs the two signal receivers 82 and 86, the two receivers 82, 86 of the monitor unit 124 may be replaced by a sole signal receiver which receives, by time sharing, the abnormal signal Seach' from the portable microsensor device 122 and the diagnosis signal Sdi and instruction signal Sin from the D-I device 118. In the latter case, the three signals Seach', Sdi Sin each are time-compressed in advance and then transmitted to the monitor unit 124 in controlled timing with each other.

A medical worker who receives, at the hospital 112, the abnormal signal Seach' of each patient 120 from his or her home 110 may be different from the doctor 138, for example, may be a nurse.

It is to be understood that the present invention may be embodied with other changes, improvements and modifications that may occur to those skilled in the art without departing from the spirit and scope of the invention defined in the appended claims.

What is claimed is:

1. A medical communication system for transmitting physical information of a living body to a medical worker, comprising:

(A) a physical information sensor device including (a1) a physical information sensor which is adapted to be worn on said living body to obtain said physical information of the living body, and generates a physical information signal representing the obtained physical information, and (a2) a first signal transmitter which transmits said physical information signal at a first output power;

(B) a first signal transmitting and receiving device including (B') a monitor unit which is adapted to be disposed near to (A) said physical information sensor device on a side of said living body, and includes (b1) a first signal receiver which receives said physical information signal from (a2) said first signal transmitter of (A) said physical information sensor device, and which receives an instruction signal representing an instruction of said medical worker directed to at least one of said living body and an attendant person for the living body, (b2) abnormality identifying means for identifying whether said physical information represented by said physical information signal received by (b1) said first signal receiver is abnormal, (b3) a second signal transmitter which transmits, at a second output power higher than said first output power, said physical information signal identified as being abnormal by (b2) said abnormality identifying means, and (b4) an instruction output device which outputs said instruction of said medical worker represented by said instruction signal received by (b1) said first signal receiver, so that said at least one of said living body and said attendant person receives the instruction; and (B") a diagnosing and informing device which is adapted to be disposed away from (B') said monitor unit, and includes (b5) a second signal receiver which receives said physical information signal from (b3) said second signal transmitter, (b6) diagnosing means for diagnosing whether said physical information represented by said physical information signal received by (b5) said second signal receiver is abnormal, (b7) a wire communication circuit including (b7-1) a third signal transmitter which transmits said physical information signal diagnosed as being abnormal by (b6) said diagnosing means, to said medical worker, via a wire communication line as a communication channel, and (b7-2) a third signal receiver which receives via said wire communication line said instruction signal representing said instruction of said medical worker in relation to said physical information represented by said physical information signal transmitted to said medical worker, and (b8) a fourth signal transmitter which transmits, to (b1) said first signal receiver, said instruction signal and a diagnosis signal representing that said physical information represented by said physical information signal received by (b5) said second signal receiver has been diagnosed as being abnormal by (b6) said diagnosing means, (B') said monitor unit further including (b9) an alarm device which issues an alarm indicating that said physical information represented by said physical information signal has been diagnosed as being abnormal by (b6) said diagnosing means, when (b1) said first signal receiver receives said diagnosis signal from (b8) said fourth signal transmitter, and (C) a second signal transmitting and receiving device which is adapted to be disposed on a side of said medical worker, and includes (c1) a fourth signal receiver which receives, via said wire communication line, said physical information signal from (b7-1) said first signal transmitter, (c2) a physical-information output device which outputs said physical information of said living body represented by said physical information signal received by (c1) said fourth signal receiver, so that said medical worker receives the physical information, (c3) an instruction input device which is operable for inputting said instruction of said medical worker and generates said instruction signal representing the input instruction of the medical worker, and (c4) a fifth signal transmitter which transmits via said wire communication line said instruction signal to (b7-2) said third signal receiver.

2. A communication system according to claim 1, wherein (b2) said abnormality identifying means of (B') said monitor unit comprises means for identifying an abnormality of a value of said physical information represented by said physical information signal which value does not fall within a reference range.

3. A communication system according to claim 1, wherein (B') said monitor unit further comprises a memory which stores a batch of physical information represented by said physical information signal received by (b1) said first signal receiver for a predetermined time duration, wherein (b3) said second signal transmitter transmits, to (b4) said second signal receiver of (B") said diagnosing and informing device, said batch of physical information stored in said memory for said predetermined time duration and including said physical information identified as being abnormal by (b2) said abnormality identifying means.

4. A communication system according to claim 3, wherein (b6) said diagnosing means of (B") said diagnosing and informing device comprises means for diagnosing an abnormality of a value of said physical information represented by said physical information which value does not fall within a normal range determined based on an average of said batch of physical information transmitted from (b3) said second signal transmitter of (B') said monitor unit to (b4) said second signal receiver.

5. A communication system according to claim 1, wherein (b7) said wire communication circuit of (B") said diagnosing and informing device comprises a modem connected to a single telephone line as said wire communication line, (b7-1) said third signal transmitter transmitting said physical information signal diagnosed as being abnormal by (b6) said diagnosing means, to said medical worker, via said telephone line, (b7-2) said third signal receiver receiving via said telephone line said instruction signal representing said instruction of said medical worker in relation to said physical information represented by said physical information signal transmitted to said medical worker.

6. A communication system according to claim 1, wherein (b7-1) said third signal transmitter and (b7-2) said third signal receiver of (B") said diagnosing and informing device of (B) said first signal transmitting and receiving device is connected via a single telephone line as said wire communication line to (c1) said fourth signal receiver and (c4) said fifth signal transmitter of (C) said second signal transmitting and receiving device.

7. The communication system according to claim 1, wherein (a1) said physical information sensor of (A) said physical information sensor device comprises at least one of a blood pressure sensor, a blood oxygen saturation sensor, a blood sugar sensor, an electrocardiograph, and a body temperature sensor.

8. A communication system according to claim 1, wherein (c2) said physical-information output device comprises an image display which displays an electrocardiogram waveform of said living body obtained by an electrocardiograph as (a1) said physical information sensor of (A) said physical information sensor device.

9. A medical communication system comprising:
(A) a portable microsensor device which is adapted to be worn on a living body, and includes
  (a1) a physical information sensor which obtains physical information of said living body, and
  (a2) a first signal transmitter which transmits, at a first output power, a physical information signal representing the obtained physical information;
(B) a monitor unit which is adapted to be disposed near to
  (A) said portable microsensor device, and includes
  (b1) a first signal receiver which receives said physical information signal from (a2) said first signal transmitter, and an instruction signal representing an instruction of a medical worker directed to said living body,
  (b2) abnormality identifying means for identifying whether said physical information represented by said physical information signal received by (b1) said first signal receiver is abnormal,
  (b3) a second signal transmitter which transmits, at a second output power higher than said first output power, said physical information signal identified as being abnormal by (b2) said abnormality identifying means, and
  (b4) an instruction output device which outputs said instruction represented by said instruction signal received by (b1) said first signal receiver;
(C) a diagnosing and informing device which is adapted to be disposed away from (B) said monitor unit, and includes
  (c1) a second signal receiver which receives said physical information signal from (b3) said second signal transmitter,
  (c2) diagnosing means for diagnosing whether said physical information represented by said physical information signal received by (c1) said second signal receiver is abnormal,
  (c3) a wire communication circuit which transmits said physical information signal diagnosed as being abnormal by (c2) said diagnosing means, to said medical worker, via a wire communication line, and receives via said wire communication line said instruction signal representing said instruction of said medical worker in relation to said physical information represented by said physical information signal transmitted to said medical worker, and
  (c4) a third signal transmitter which transmits, to (b1) said first signal receiver, said instruction signal and a diagnosis signal representing that said physical information represented by said physical information signal received by (c1) said second signal receiver has been diagnosed as being abnormal by (c2) said diagnosing means,
(B) said monitor unit further including
  (b5) an alarm device which issues an alarm indicating that said physical information represented by said physical information signal has been diagnosed as being abnormal by (c2) said diagnosing means, when (b1) said first signal receiver receives said diagnosis signal from (c4) said third signal transmitter.

10. A medical communication system according to claim 9, wherein (b2) said abnormality identifying means of (B) said monitor unit comprises means for identifying an abnormality of a value of said physical information represented by said physical information signal which value does not fall within a reference range.

11. A medical communication system according to claim 9, wherein (B) said monitor unit further comprises a memory which stores a batch of physical information represented by said physical information signal received by (b1) said first signal receiver for a predetermined time duration, wherein (b3) said second signal transmitter transmits, to (c1) said second signal receiver of (C) said diagnosing and informing device, said batch of physical information stored in said memory for said predetermined time duration and including said physical information identified as being abnormal by (b2) said abnormality identifying means.

12. A medical communication system according to claim 11, wherein (c2) said diagnosing means of (C) said diagnosing and informing device comprises means for diagnosing an abnormality of a value of said physical information represented by said physical information which value does not fall within a normal range determined based on an average of said batch of physical information transmitted from (b3) said second signal transmitter of (B) said monitor unit to (c1) said second signal receiver.

13. A communication system according to claim 9, wherein (c3) said wire communication circuit of (C) said diagnosing and informing device comprises (c3-1) a modem connected to a single telephone line as said wire communication line, (c3-2) a third signal transmitter transmitting said physical information signal diagnosed as being abnormal by (c2) said diagnosing means, to said medical worker, via said telephone line, and (c3-3) a third signal receiver receiving via said telephone line said instruction signal representing said instruction of said medical worker in relation to said physical information represented by said physical information signal transmitted to said medical worker.

14. A medical communication system according to claim 9, wherein (a1) said physical information sensor of (A) said portable microsensor device comprises at least one of a blood pressure sensor, a blood oxygen saturation sensor, a blood sugar sensor, an electrocardiograph, and a body temperature sensor.

* * * * *